United States Patent
Sakai et al.

(10) Patent No.: US 8,123,688 B2
(45) Date of Patent: Feb. 28, 2012

(54) ULTRASOUND DIAGNOSIS APPARATUS

(75) Inventors: Ryoichi Sakai, Mitaka (JP); Akimitsu Harada, Mitaka (JP)

(73) Assignee: Hitachi Aloka Medical, Ltd., Mitaka-shi, Tokyo (JP)

( * ) Notice: Subject to any disclaimer, the term of this patent is extended or adjusted under 35 U.S.C. 154(b) by 1176 days.

(21) Appl. No.: 11/869,238

(22) Filed: Oct. 9, 2007

(65) Prior Publication Data

US 2008/0086055 A1    Apr. 10, 2008

(30) Foreign Application Priority Data

Oct. 10, 2006 (JP) ................. 2006-276121

(51) Int. Cl.
*A61B 8/00* (2006.01)
(52) U.S. Cl. ........ 600/437; 600/407; 600/439; 600/441; 600/443; 600/448
(58) Field of Classification Search .................. 600/407, 600/437–448
See application file for complete search history.

(56) References Cited

U.S. PATENT DOCUMENTS

| | | | |
|---|---|---|---|
| 5,493,788 A | 2/1996 | Richardson | |
| 5,558,091 A | 9/1996 | Acker et al. | |
| 5,588,435 A | 12/1996 | Weng et al. | |
| 5,953,073 A | 9/1999 | Kozina et al. | |
| 6,569,098 B2 * | 5/2003 | Kawchuk ..................... | 600/437 |
| 2005/0148860 A1 * | 7/2005 | Liew et al. .................... | 600/410 |
| 2006/0074311 A1 | 4/2006 | Sakai et al. | |

FOREIGN PATENT DOCUMENTS

| | | |
|---|---|---|
| EP | 1523940 A1 | 4/2005 |
| EP | 1707124 A2 | 1/2006 |
| EP | 1693004 A1 | 8/2006 |
| JP | 7-222742 A | 8/1995 |
| JP | 9-503410 A | 4/1997 |
| JP | 10-503671 A | 4/1998 |
| JP | 2001231788 A | 8/2001 |
| JP | 2001309918 A | 11/2001 |
| JP | 2002-34986 A | 2/2002 |
| JP | 2004-157815 A | 6/2004 |
| JP | 2004298205 A | 10/2004 |
| JP | 2005-102945 A | 4/2005 |
| JP | 2005-152079 A | 6/2005 |
| JP | 2005152079 A | 6/2005 |
| WO | 95/35062 A2 | 12/1995 |

OTHER PUBLICATIONS

European Search Report dated Feb. 4, 2008, issued in corresponding European Patent Application No. 07019540.

(Continued)

*Primary Examiner* — Brian Casler
*Assistant Examiner* — Joel Lamprecht
(74) *Attorney, Agent, or Firm* — Westerman, Hattori, Daniel & Adrian, LLP

(57) ABSTRACT

An angle calculating unit calculates a bending angle of a bone based on a plurality of surface points. A characteristic data calculating unit determines an indication value which reflects a load applied on the bone, a bone length of the bone, and a position of a fractured part. The characteristic data calculating unit calculates, as characteristic data reflecting a mechanical characteristic of the bone, a proportionality constant indicating a ratio between the indication value and the bending angle of the bone.

16 Claims, 10 Drawing Sheets

OTHER PUBLICATIONS

Japanese Office Action dated Jul. 13, 2010, issued in corresponding Japanese Patent Application No. 2006-117541.
Japanese Office Action dated Sep. 30, 2008 (mailed date), issued in corresponding Japanese Application No. 2006-276121.
Office Action dated Oct. 29, 2009, issued in U.S. Appl. No. 11/835,819.
Office Action dated Apr. 29, 2010, issued in U.S. Appl. No. 11/835,819.

* cited by examiner (1) NO LOAD (2) LOADED

ULTRASOUND DIAGNOSIS APPARATUS

BACKGROUND

1. Technical Field

The present invention relates to a technique for evaluating bone using ultrasound.

2. Description of the Related Art

An easy means for quantitative measurement of mechanical characteristics of bone is desired for evaluating, for example, the state of joining of a bone fracture. In related art, X-ray photography is widely used for evaluating the state of a bone fracture. However, because an image of a callus which is growing in the diseased area cannot be clearly captured with X-ray photography, quantitatively diagnosing the degree of joining remains difficult. The measurement of mechanical characteristics of bone is not limited to a fractured bone, and may be executed on healthy bone tissue. For example, a measurement of the bone strength or the like of a healthy bone can be useful in the diagnosis of osteoporosis or the like.

There are known methods for quantitatively evaluating mechanical characteristics of bone without the use of X-ray photography including, for example, a strain gauge method in which a strain gauge is mounted on an external fixator and the strain of the external fixator is measured; a vibration wave method in which a vibration is applied to a bone from outside and a characteristic frequency is evaluated; and an acoustic emission method in which acoustic waves generated by a bone which has reached yield stress are detected. These methods, however, have various problems in that a limitation is imposed on the treatment to which these methods can be applied, that the bone is subjected to an invasive procedure, and that the precision of the quantitative evaluation is insufficient.

In view of the above circumstances, an apparatus for measuring a curing state of a diseased part of a bone using an ultrasound has been proposed in order to enable measurement which is noninvasive to the bone (JP 2005-152079 A).

JP 2005-152079 A discloses a technique in which an angle of two bone pieces sandwiching the fractured part is measured by transmitting and receiving an ultrasound to and from a bone, and characteristic information reflecting the mechanical characteristics of the bone is generated based on the angle.

The inventors of the present application have studied a new evaluation technique improving the epoch-making technology described in JP 2005-152079A. In addition, the present inventors have studied a display technique of a measurement result obtained using the epoch-making technology described in JP 2005-152079 A.

SUMMARY

The present invention was conceived in view of the above-described circumstances, and an advantage of the present invention is that an improved technique for evaluating mechanical characteristics of a target bone using an ultrasound is provided. Another advantage of the present invention is that a technique for displaying a measurement result of a bone shape measured using an ultrasound in an easily understandable manner is provided.

According to one aspect of the present invention, there is provided an ultrasound diagnosis apparatus comprising a transmission and reception unit which forms a plurality of ultrasonic beams on a target bone, a surface point identifying unit which identifies a surface point corresponding to a surface of the target bone for each ultrasonic beam, an angle calculating unit which calculates a bending angle of the target bone based on a plurality of surface points, and a characteristic information generator unit which generates characteristic information which reflects a mechanical characteristic of the target bone based on a bending angle of the target bone due to an external action and form data which is unique to the target bone.

With the above-described structure, a bone can be evaluated in consideration of form data which is unique to the target bone. Because of this, for example, bone can be evaluated while influences of individual differences due to a difference in form (which may include a shape) are reduced.

According to another aspect of the present invention, it is preferable that, in the ultrasound diagnosis apparatus, the characteristic information generator unit uses, as the form data, a length of bone of the target bone and a position of an evaluation reference point of the target bone. When the target bone is a bone with a fractured part, for example, the fractured part is set as the evaluation reference point. In the case of a bone with a fractured part, typically, the fractured part is likely a bending part (vertex of bend). When the target bone is a healthy bone, for example, a weak part of the bone (which is likely to bend) may be determined based on palpation and image diagnosis, etc. and may be set as the evaluation reference point. Alternatively, it is also possible to simply set a center portion of the bone as the evaluation reference point.

DETAILED DESCRIPTION

Figure 1:
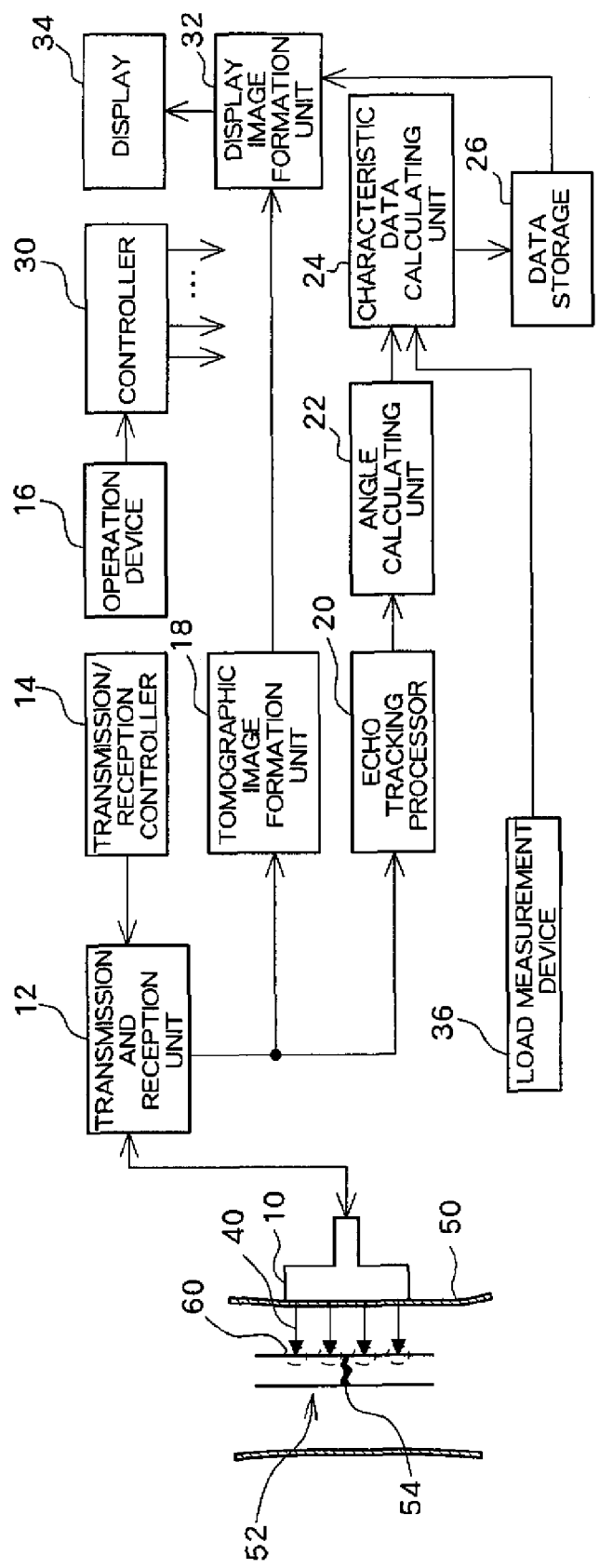
FIG. 1 is a block diagram showing an overall structure of an ultrasound diagnosis apparatus according to a preferred embodiment of the present invention.

FIG. 1 illustrates a preferred embodiment of an ultrasound diagnostic apparatus according to the present invention. FIG. 1 is a block diagram showing an overall structure of the ultrasound diagnostic apparatus. A probe 10 is an ultrasonic probe which is used in contact with a surface of the body of a subject 50. The probe 10 forms a plurality of ultrasonic beams 40 directed towards a bone 52 within the body of the subject 50. In this process, for example, a plurality of ultrasonic beams 40 are formed on each of two upper and lower bone pieces sandwiching a fractured part 54 of the bone 52. Surface points 60 which are set on a surface of the bone 52 will be described later in more detail.

Figure 2:
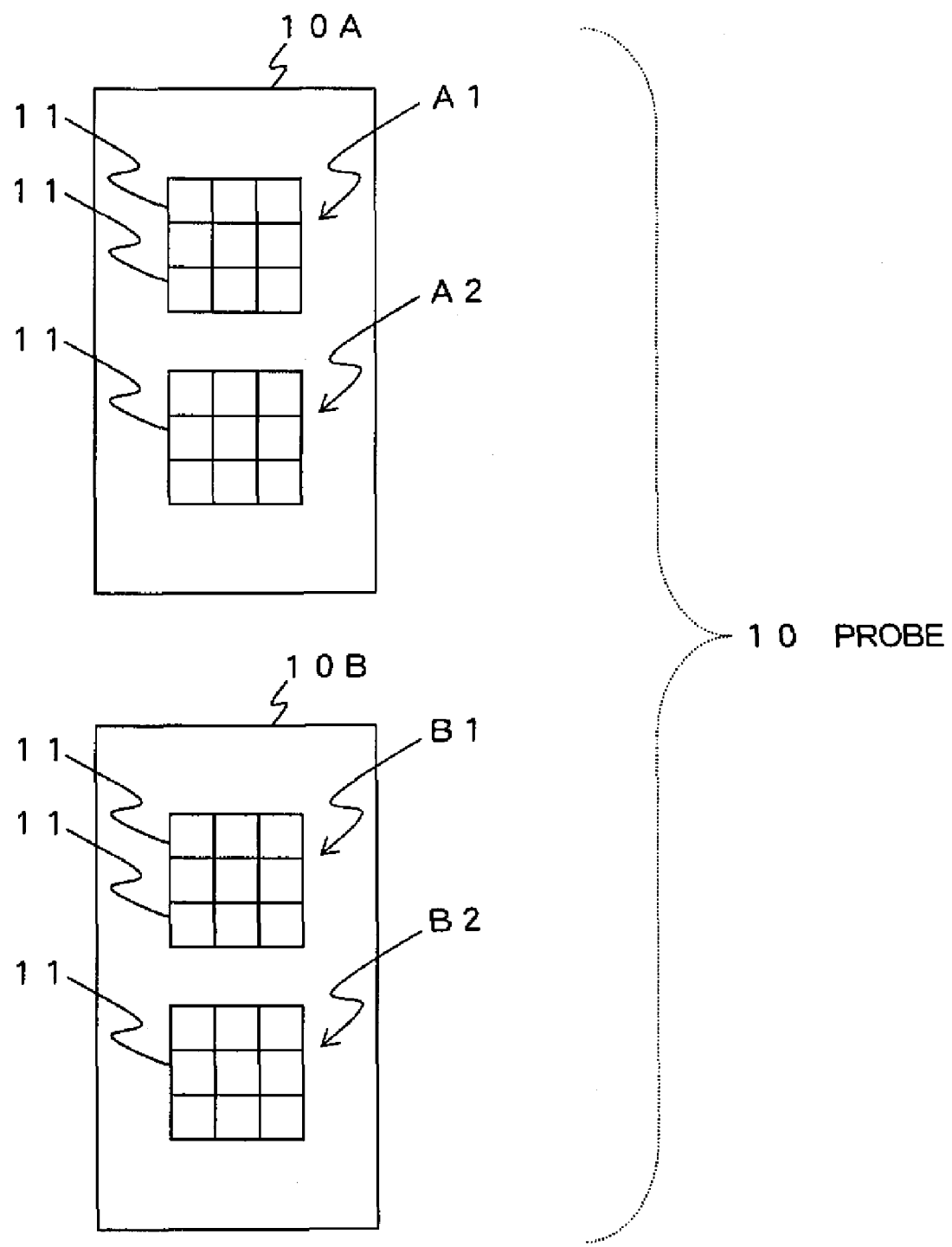
FIG. 2 is a diagram for explaining a preferable probe in an ultrasound diagnosis apparatus according to a preferred embodiment of the present invention.

FIG. 2 is a diagram for explaining a probe 10 which may be preferably employed with the ultrasound diagnosis apparatus of the present embodiment. The probe 10 comprises a probe pair including a probe 10A and a probe 10B. The probe 10A comprises, within the probe 10A, a subarray A1 and a subarray A2, each of which comprising nine transducer elements 11. The probe 10B comprises, within the probe 10B, a subarray B1 and a subarray B2, each of which comprising nine transducer elements 11.

An echo tracking ultrasonic beam (which will be described later) is formed for each subarray. For example, for each subarray, one of the transducer elements 11 of the array is driven and an ultrasonic beam is formed. Alternatively, it is also possible to form an ultrasonic beam by driving a plurality of transducer elements 11 for each subarray.

In this manner, four echo tracking ultrasonic beams are formed by subarrays A1-B2. During this process, two ultrasonic beams fare formed by the probe 10A on one of the upper and lower bone pieces sandwiching the fractured part (reference numeral 54 in FIG. 1) of the bone (reference numeral 52 in FIG. 1) and two ultrasonic beams are formed by the probe 10B on the other one of the two bone pieces.

The probe 10 used in the ultrasound diagnosis apparatus of the present embodiment is not limited to the probe pair type probes as shown in FIG. 2. The probe may alternatively be, for example, a linear electronic scan probe (linear probe) which electronically scans an ultrasonic beam.

Referring again to FIG. 1, a transmission and reception unit 12 controls the probe 10 to electronically scan the ultrasonic beam 40 in a tomographic surface (cut surface of the subject 50, that is, a longitudinal cross section of the bone 52, in FIG. 1). When the probe 10 is a linear probe, for example, 120 ultrasonic beams 40 (FIG. 1 only shows four echo tracking ultrasonic beams 40 to be described later in detail) are sequentially electronically scanned and an echo signal is obtained for each ultrasonic beam 40. A plurality of obtained echo signals are output to a tomographic image formation unit 18, and the tomographic image formation unit 18 forms a tomographic image (B mode image) of the bone based on the plurality of the echo signals. The formed B mode image is displayed on a display 34 through a display image formation unit 32.

The echo signal obtained at the transmission and reception unit 12 is also output to an echo tracking processor 20. The echo tracking processor 20 applies an echo tracking process in which a bone surface portion is extracted from each echo signal and is tracked. For the echo tracking process, a technique detailed in JP2001-309918A, for example, is used. A summary of this technique will now be described.

The echo signal obtained from the probe 10 has a large amplitude in a portion corresponding to the bone surface. When the bone surface portion is captured simply as a portion with a large amplitude, it is not clear as to which part of a range of the large amplitude corresponds to the surface portion, and, as a result, an extraction error occurs in a degree equivalent to the range of the large amplitude (which is approximately 0.2 mm in a typical ultrasound diagnosis apparatus). In the echo tracking process, a zero-cross point is detected as a representative point of the echo signal, and the detected zero-cross point is tracked so that the extraction precision is significantly improved (the precision can be improved to as much as approximately 0.002 mm). The zero-cross point is detected as a timing in a tacking gate period in which a polarity of an amplitude of the echo signal changes from positive to negative or from negative to positive. When a zero-cross point is detected, a new tracking gate is set with the detected zero-cross point as a center. For the echo signal obtained at the next timing, a zero-cross point is detected within the newly set tracking gate period. In this manner, the zero-cross point of the echo signal is tracked as a surface point 60 for each ultrasonic beam, and the position of the bone surface is highly precisely measured with the probe 10 as a reference.

For the echo tracking process, four tracking echo signals, for example, are used. The tracking echo signal may be selected from among the echo signals used for the tomographic image formation (for example, 120 echo signals) or, alternatively, the tomographic image formation may be interrupted and four tracking echo signals only may be obtained.

An angle calculating unit 22 sets, based on surface points 60 extracted by echo tracking processor 20, a line corresponding to each of the two upper and lower bone pieces sandwiching the fractured part 54 of the bone 52. The angle calculating unit 22 then calculates an angle between two lines corresponding to the two bone pieces. The setting process of the line and the angle calculation process in the angle calculating unit 22 will now be described with reference to FIG. 3. Elements corresponding to those shown in FIG. 1 are assigned the same reference numerals as FIG. 1.

Figure 3:
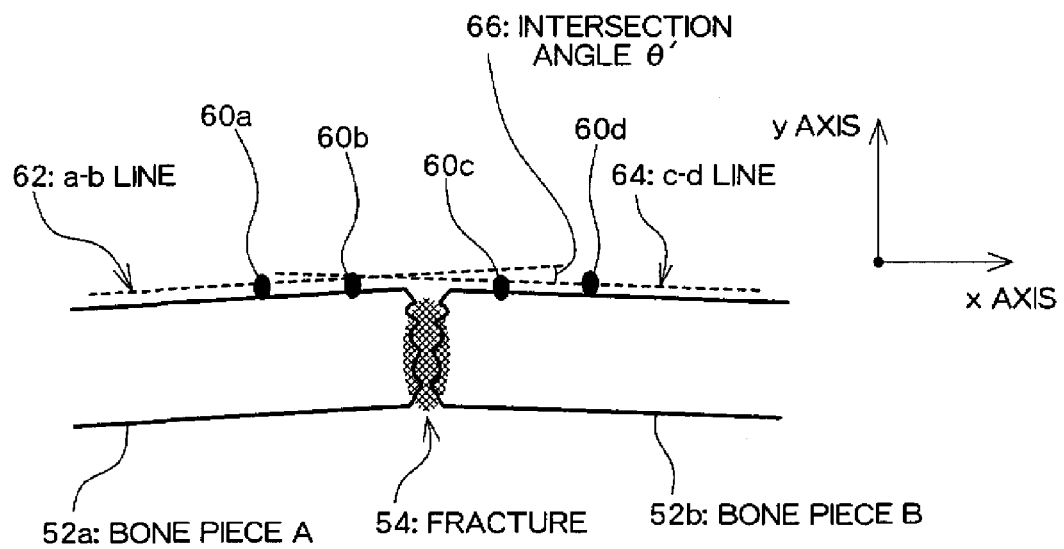
FIG. 3 is a diagram for explaining a setting process of lines and an angle calculation process between the lines.
Figure 3:
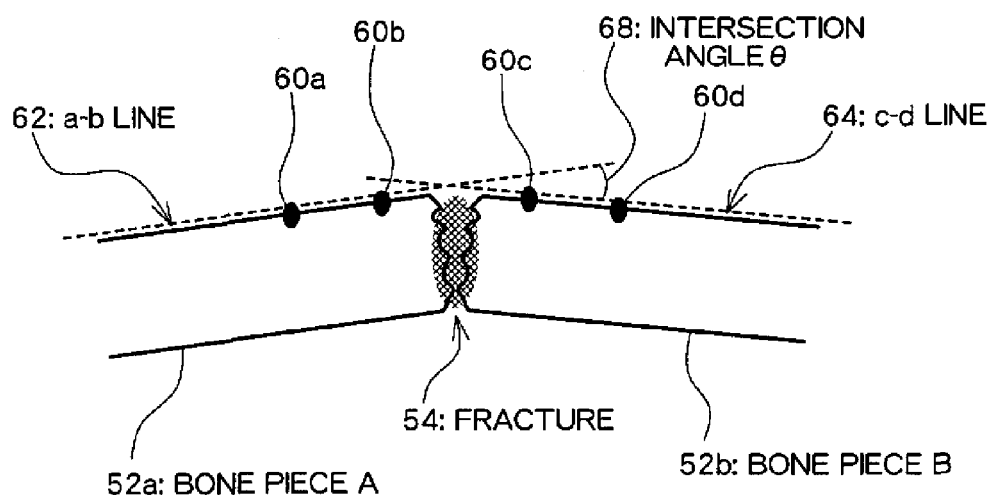

FIG. 3 is a diagram for explaining a setting process of a line corresponding to each of the two bone pieces and an angle calculation process between the lines. FIG. 3(1) shows an enlarged view of the fractured part 54 when no load is applied and FIG. 3(2) shows an enlarged view of the fractured part 54 when a force is applied due to a load. The bone piece A 52a in FIG. 3 corresponds to a bone piece above the fractured part 54 in FIG. 1 and the bone piece B 52b in FIG. 3 corresponds to a bone piece below the fractured part 54 in FIG. 1. In addition, four surface points (60a-60d) in FIG. 3 correspond to the surface points 60 in FIG. 1. In FIG. 3, the horizontal direction is defined as an x-axis direction and the vertical direction is defined as a y-axis direction.

The four surface points (60a-60d) are set, for example, corresponding to the position of the fractured part 54. For this purpose, for example, the examiner sets two measurement points near a surface of the bone piece A 52a and two measurement points near a surface of the bone piece B 52b while checking the position of the fractured part 54 based on the B mode image of the bone displayed on the display 34. The four measurement points are set from an operation device 16, through a controller 30, and in a transmission/reception controller 14. The transmission/reception controller 14 forms four tracking ultrasonic beams 40 having the four measurement points as the focus points, the surface points of the bone are tracked in the echo tracking processor 20, and the positions of the surface points (60a-60d) are highly precisely measured with the probe 10 as a reference. Alternatively, it is also possible to employ a configuration in which, in the setting of the measurement points, the examiner only designates a position of the fractured part 54 and the transmission/reception controller 14 sets the positions of the four measurement points in the x-axis direction.

The angle calculating unit 22 sets a line connecting two surface points 60a and 60b, which are extracted by the echo tracking processor 20, as an a-b line 62 corresponding to the bone piece A 52a. Similarly, the angle calculating unit 22 sets a line connecting two surface points 60c and 60d as a c-d line 64 corresponding to the bone piece B 52b. Data of the a-b line 62 and the c-d line 64 measured by the angle calculating unit 22 (for example, an equation of the lines in a coordinate system having the reference at the probe 10) is recorded in a data storage 26 through a characteristic data calculating unit 24. The data of the a-b line 62 and the c-d line 64 are recorded in the data storage 26 both for the state of no load of FIG. 3(1) and for the loaded state of FIG. 3(2). Alternatively, for the loaded state, the data may be recorded in the data storage 26 for each load value.

The angle calculating unit 22 further calculates an intersection angle between the a-b line 62 and the c-d line 64 based on the data of the a-b line 62 and the c-d line 64. In other words, the angle calculating unit 22 calculates an intersection angle θ' 66 between the two lines based on the data of the a-b line 62 and the c-d line 64 when no load is applied. The angle calculating unit 22 also calculates an intersection angle θ 68 based on data of the a-b line 62 and the c-d line 64 for each load value. As shown in FIGS. 3(1) and 3(2), when a pressure is applied to apply a load, the intersection angle between the two lines changes. The intersection angle θ 68 calculated for each load value is recorded as a bending angle in the data storage 26 through the characteristic data calculating unit 24. The angle calculating unit 22 may calculate a difference between the intersection angle θ 68 and the intersection angle θ' 66 for each load value.

In FIG. 3, a bend is shown in a direction in which the fractured part 54 moves along a positive direction of the y-axis. Alternatively, the angle may be measured through the above-described principle for a bend in a direction in which the fractured part 54 moves along a negative direction of the y-axis.

Although measurement of the bone 52 including the fractured part 54 has been described with reference to FIGS. 1 and 3, the present embodiment is not limited to such a configuration, and a bone 52 having no bone fracture may be measured. In the case of a bone 52 without a fracture (healthy bone), a measurement point (evaluation reference point) corresponding to the fractured part 54 may be set and the measurement point (evaluation reference point) may be assumed to be a bend part and the bending angle may be calculated through the principle described above with reference to FIG. 3. For a healthy bone, it is also possible, for example, to determine a weak portion (a part which tends to bend) of the bone based on palpation or image diagnosis, and set the weak point as the measurement point. Alternatively, it is also possible to employ a simple configuration in which a center portion of the bone is set as the measurement point.

The load to be applied to the bone 52 is applied along an approximate vertical direction with respect to the axis near the fractured part 54 by supporting both ends of the bone 52 along the axial direction. In other words, a three-point loading method is employed in which both ends are supported and a load is applied near the fractured part 54. In this process, the amount of load or the like should be carefully set according to the state of the bone 52. Alternatively, it is also possible to employ a loading method in which a load is applied along the axial direction of the bone 52.

Referring again to FIG. 1, when a bending angle of the bone 52 is determined, the characteristic data calculating unit 24 calculates characteristic data reflecting a mechanical characteristic of the bone 52 based on the bending angle of the bone 52 due to the load and on form data which is unique to the bone 52. As the form data, for example, a length of bone (bone length) of the bone 52 and a position of the fractured part 54 are used.

Figure 4:
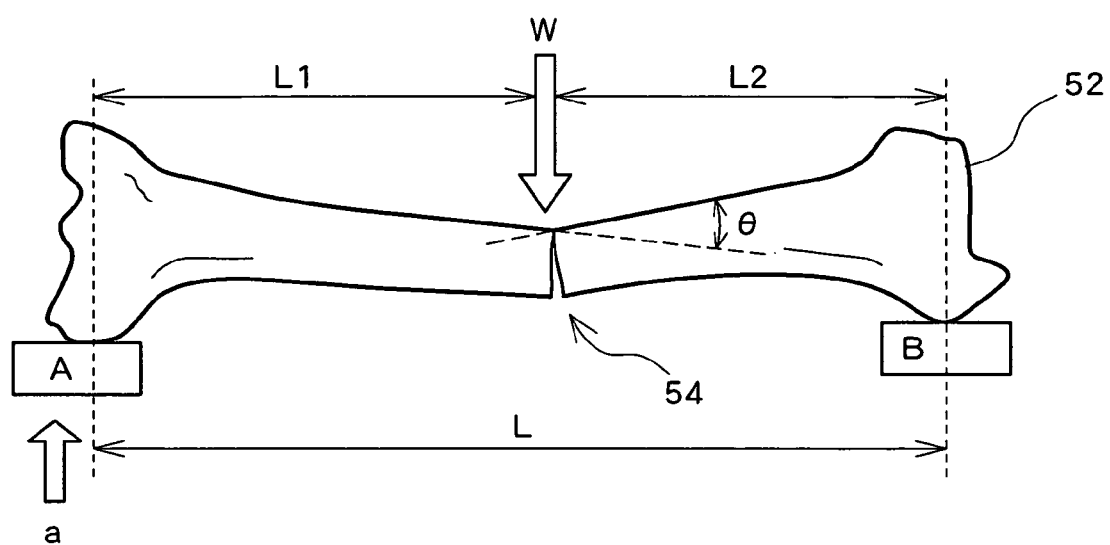
FIG. 4 is a diagram for explaining a relationship among the bone, bending angle, and form data.

FIG. 4 is a diagram for explaining a relationship among the bone, bending angle, and form data. The bone 52 is, for example, tibia, and ends of the bone 52 along the axial direction are supported by pivots A and B. When the bone 52 is a tibia, for example, a fibular head on a side near the fibula and an external ankle are supported by pivots A and B. A load W which is approximately vertical with respect to the axial direction of the bone 52 is applied to the position of the fractured part 54.

Although tissues of the subject other than the bone 52 are not shown in FIG. 4, the pivots A and B support the bone 52 through the body surface of the subject and the load W is applied from the body surface of the subject.

In FIG. 4, a bone length L is a length of the bone 52 along the axial direction. When the bone 52 is a tibia, for example, a distance from the fibular head on the side near the fibula to the external angle is set as the bone length L. Distances L1 and L2 are distances from the ends of the bone 52 to the fractured part 54, respectively. The form data such as the bone length L and the distances L1 and L2 may be measured, for example, by the examiner through palpation or the like or may be measured using the ultrasonic B mode image. Alternatively, it is also possible to use an imaging device such as an X-ray (roentgen), CT, or MRI device.

When a load W is applied to the bone 52, a load is applied to the ends of the bone 52 from the pivots A and B. In FIG. 4, the load a is a load applied to the pivot A. The bending angle θ is a bending angle of the bone 52 when the load W is applied, with the fractured part 54 being a vertex of the bend.

A calculation process in the characteristic data calculating unit 24 of FIG. 1 will now be described with reference to FIG. 4. The characteristic data calculating unit 24 refers to the load value (load W) measured by a load measurement device 36. As described before, the bending angle θ is calculated by the angle calculating unit 22. The bending angle θ is a parameter which reflects a mechanical characteristic of the bone 52 (such as a degree of bone union of the fractured part 54), and is proportional to an internal stress σ acting on the fractured part 54. In other words, the following equation holds:

$$\theta \propto \sigma \quad \text{[Equation 1]}$$

The internal stress σ is a parameter which is proportional to a bending moment M acting on the fractured part 54, and, thus, the following equation holds:

$$\sigma \propto M \quad \text{[Equation 2]}$$

In addition, the bending moment M is a product of the load a applied on the pivot A and the distance L1 to the fractured part 54:

$$M = a \times L1 \quad \text{[Equation 3]}$$

Because of the balance of the forces, a=W×L2/L, and, thus, Equation 3 can be converted into the following:

$$M = W \times L2 \times L1 / L \quad \text{[Equation 4]}$$

The following Equation 5 can then be derived from Equations 1, 2, and 4:

$$\theta \propto W \times L2 \times L1 / L \quad \text{[Equation 5]}$$

The right side of Equation 5 is an indication value which takes into account a load W applied to the bone 52, the bone length L, and the position of the fractured part 54 (distances L1 and L2). Equation 5 indicates that this indication value is proportional to the bending angle θ. If a proportionality constant representing the proportionality relationship is taken as ET-stiffness, the following Equation 6 can be obtained:

$$ET\text{-stiffness} = (W \times L2 \times L1)/(L \times \theta) \quad \text{[Equation 6]}$$

The characteristic data calculating unit 24 calculates the proportionality constant ET-stiffness which can be obtained based on the bending angle θ of the bone 52 due to the load W and the form data which is unique to the bone 52 (bone length L and distances L1 and L2) as characteristic data reflecting the mechanical characteristic of the bone 52, and stores the calculation result in the data storage 26.

Because L2=L−L1, the ET-stiffness can be calculated by measuring only the bone length L and the distance L1 as the form data. As the bending angle θ, the intersection angle θ 68 for a loaded case shown in FIG. 3 may be used or an angle difference between the intersection angle θ 68 and the intersection angle θ' 66 may be used. Alternatively, it is also possible to describe the position of the load W with distances L1' and L2', and apply an analysis in consideration of the distances L1' and L2'. In the case of the healthy bone, for example, an analysis may be applied in consideration of an amount of flexure.

As described before, the display image formation unit 32 forms a display image based on the B mode image (data) formed by the tomographic image formation unit 18, and displays the display image on the display 34. The display image formation unit 32 can also numerically display data such as the proportionality constant ET-stiffness stored in the data storage 26. In addition, the display image formation unit 32 forms an input screen for the examiner to input the form data of the bone 52 (bone length L and distances L1 and L2), and displays the input screen on the display 34.

Figures 5, 6:
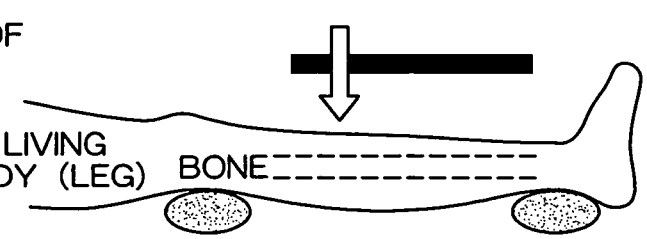
FIG. 5 is a diagram showing a first example screen of an input screen formed by a display image formation unit.
FIG. 6 is a diagram showing a second example screen of an input screen formed by a display image formation unit.

FIG. 5 is a diagram showing a first example display of the input screen formed by the display image formation unit. In the input screen of FIG. 5, input boxes corresponding to a subject name, a subject ID, a bone length, and a position of the fractured part, respectively, are provided. The examiner inputs the data in these input boxes using an operation device such as a keyboard and a touch panel (reference numeral 16 of FIG. 1). FIG. 5 shows a state in which "330" mm is input as the bone length and "150" mm is input as a position of the fractured part. The position of the fractured part is described by the distance L1 or the distance L2 of FIG. 4.

When necessary data are input in the input boxes, the examiner operates on an "analyze" button provided in the input screen of FIG. 5, and the characteristic data calculating unit (reference numeral 24 of FIG. 1) calculates the proportionality constant ET-stiffness.

FIG. 6 is a diagram showing a second example display of the input screen formed by the display image formation unit. In the input screen of FIG. 6, input boxes corresponding to a subject name, a subject ID, and a bone length, respectively, are provided. The functions of these input boxes and the method of use are identical to those for the input boxes of the corresponding names of FIG. 5.

In the input screen of FIG. 6, an image of the subject (living body) including the bone and a cursor (arrow) which moves along the image are provided. The examiner moves the cursor to a position of the image corresponding to the fractured part using the operation device (reference numeral 16 of FIG. 1) such as a mouse and a trackball, and determines the position of the cursor. Through this process, the position of the fractured part is input.

The image of the living body including the bone is, for example, the ultrasonic B mode image or the X-ray image. The examiner can examine the fractured part displayed as an image while viewing the image of the living body, and set the cursor on the position of the fracture part.

It is also possible to numerically display, in the input screen, a position of the fractured part which is input through the cursor. It is also possible to employ an input form in which the cursor is not displayed and only the image of the living body including the bone is displayed, and the position of the fractured part is marked with the mouse or the like on the image of the living body. In this case, a marker may be displayed at a position indicated by the mouse.

It is also possible to employ a configuration in which a height of the subject is input in place of the bone length, and the bone length is calculated based on the height. When analysis in consideration of the position of the load W is to be applied, it is possible to provide an input box for inputting the position of the load W in the input screen.

In the above-described embodiment, the proportionality constant ET-stiffness which can be obtained based on the bending angle θ of the bone 52 due to the load W and form data which is unique to the bone 52 (bone length L and distances L1 and L2) is calculated. In other words, evaluation of bone is enabled which considers the form data which is unique to the bone. With this structure, for example, evaluation of bone is enabled in which the influences of individual differences of the bone due to differences in the bone length and in the position of the fractured part are reduced, and, as a result, the evaluation result can be generalized, for example, and the precision of the comparative evaluation between subjects with different bone forms (for example, between an adult and a child or between a male and female) can be improved.

Next, a technique for displaying the measurement result of the bone shape in an easily understandable manner in the present embodiment will be described with reference to FIG. 1.

The characteristic data calculating unit 24 generates measurement data in which a measured quantity, an amount of load, and time when a load is applied to the bone are correlated to each other, and stores the measurement data in the data storage 26. An amount of displacement of each surface point and a bending angle of the bone, etc. are supplied from the angle calculating unit 22 to the characteristic data calculating unit 24. In addition, a measurement result of a load value due to the application of the load on the bone 52 is supplied from the load measurement device 36 to the characteristic data calculating unit 24. The characteristic data calculating unit 24 correlates the amount of displacement of each surface point, the bending angle of the bone, and the load value during the loading process, and further correlates the time when the load value is applied, to generate the measurement data. The time is identified using, for example, time information obtained by the controller 30 or the like.

Figure 7:
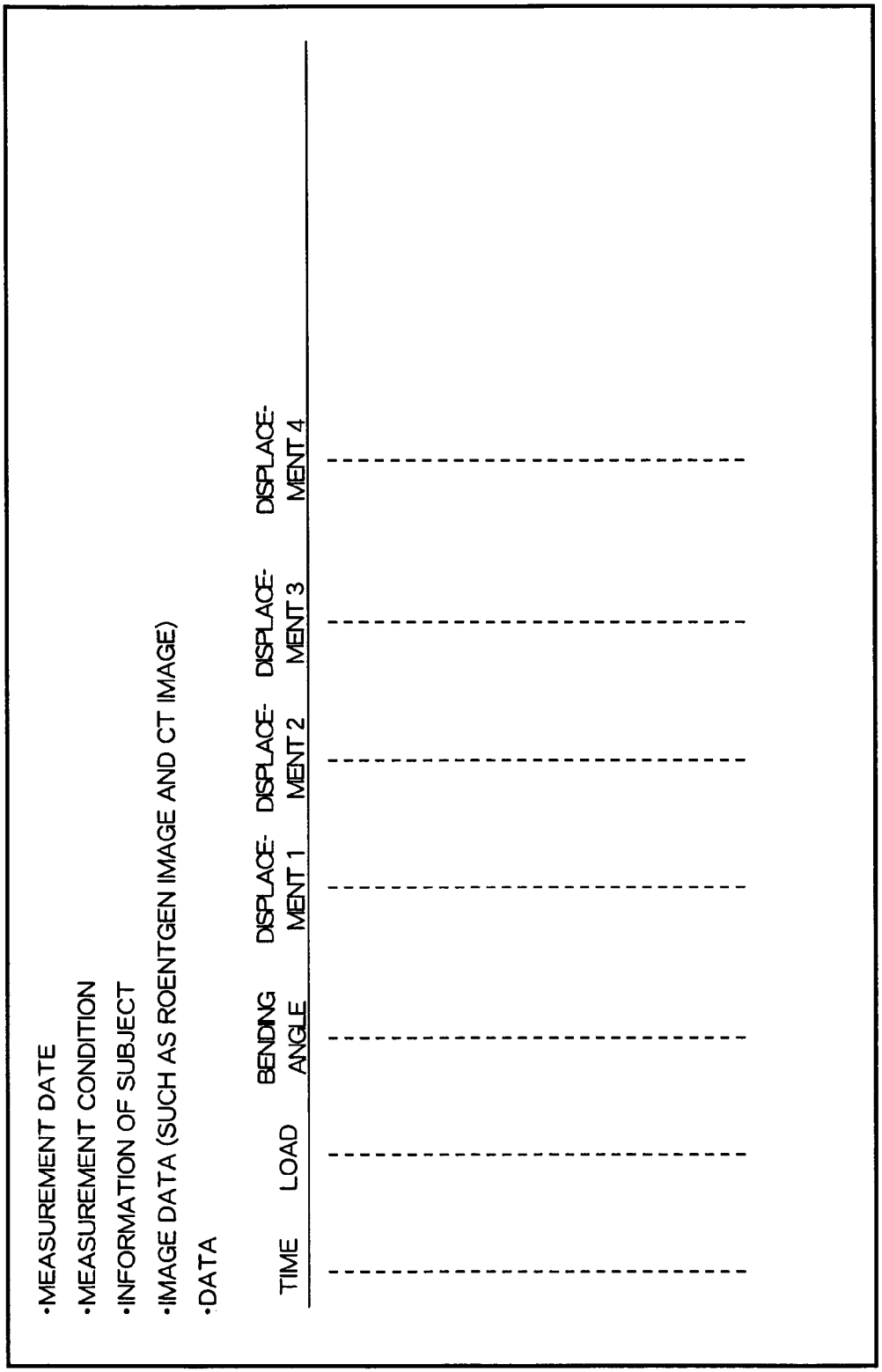
FIG. 7 is a diagram for explaining measurement data.

FIG. 7 is a diagram for explaining measurement data which is generated by the characteristic data calculating unit and stored in the data storage. The measurement data includes the measurement date and time (including year, month, and day) when the data is measured, a measurement condition, and subject information. Alternatively, it is also possible to employ a configuration in which image data or the like of the bone which is the measurement target is attached. The image data is preferably, for example, a tomographic image formed by the tomographic image formation unit (reference numeral 18 of FIG. 1). Alternatively, data such as the X-ray image and the CT image may be attached as the image data. The image data itself may be attached to the measurement data, or, alternatively, an address of storage location of the image data or the like may be attached as link information.

The time when the load value is applied (time), the load value (load), the bending angle of the bone (bending angle), and amounts of displacements of the surface points (displacements 1-4) are arranged horizontally and correlated to each other. The displacements 1-4 are displacements of bone surface points obtained based on the four tracking beams. Alternatively, it is also possible to employ a configuration in which the measured quantity such as an amount of strain of the bone is correlated subsequent to the value of the displacement 4. In this manner, the time, load, bending angle, etc. are arrange horizontally and correlated, and data for different times are arranged along the vertical direction.

With reference again to FIG. 1, the display image formation unit 32 forms a measurement result image for displaying a measured quantity, based on measurement data stored in the data storage 26. In addition, the display image formation unit 32 switches between the tomographic image formed by the tomographic image formation unit 18 and the measurement result image or forms a display image in which the tomographic image and the measurement result image are arranged side by side. The formed display image is displayed on the display 34.

A characteristic of an ultrasound diagnosis apparatus of the present embodiment is the measurement result image formed by the display image formation unit 32. The measurement result image formed in the present embodiment will now be described with reference to FIGS. 8-12.

Figure 8:
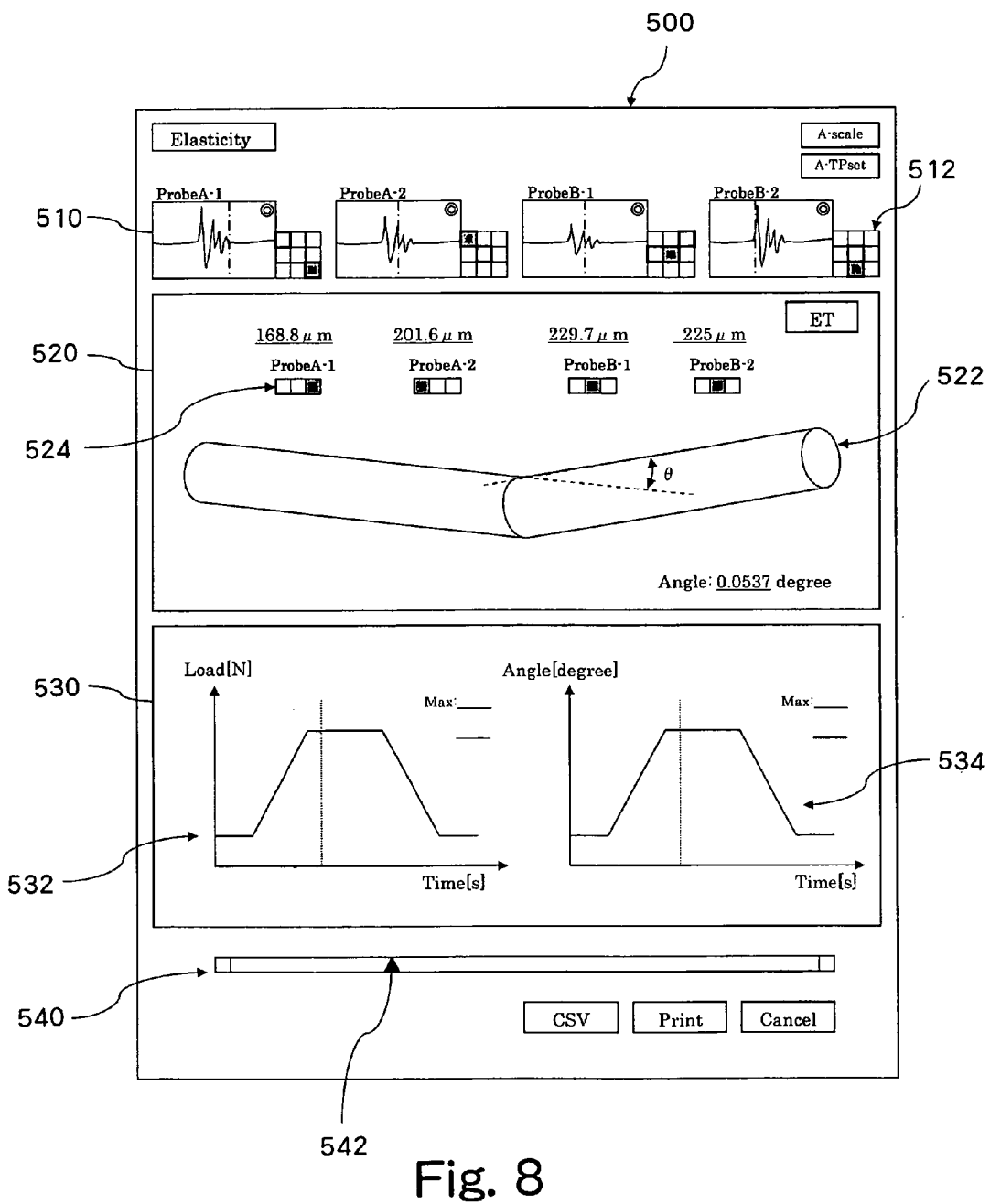
FIG. 8 is a diagram for explaining an example display of a measurement result image.

FIG. 8 is a diagram for explaining an example display of the measurement result image. A measurement result image 500 shown in FIG. 8 includes a waveform image 510, a bone shape image 520, a graph image 530, and a time setting bar 540.

The waveform image 510 shows a waveform near a surface point of each ultrasonic beam. As described before with reference to FIGS. 1 and 2, in the present embodiment, four echo tracking ultrasonic beams are formed. In FIG. 8, the waveform image 510 shows four waveforms of ProbeA-1, ProbeA-2, ProbeB-1, and ProbeB-2. These four waveforms correspond to the waveforms of the ultrasonic beams formed by the subarrays A1, A2, B1, and B2 of FIG. 2, respectively.

On each of the four waveforms in FIG. 8, a tracking point designating marker shown with a dot-and-chain line is displayed. The position of the tracking point in the waveform can be understood with the marker. A beam position image 512 is displayed adjacent to each waveform.

The beam position image 512 shows a position of an ultrasonic beam in each subarray. For example, when an ultrasonic beam is formed by driving only one transducer element (reference numeral 11 of FIG. 2) in the array for each subarray, the position of the driven transducer element is shown in the beam position image 512. For example, the portion of the driven transducer element is displayed in a display form which differs from that for the other portions. In FIG. 8, the portion of the driven transducer element is represented with a filled box.

An auto-scale switch (A-scale) for waveform display and an automatic setting switch (A-TPset) for the tracking point may be provided near the waveform image 510 or the beam position image 512.

The bone shape image 520 visually represents a bent state of a bone according to the bending angle. A bone image 522 in the bone shape image 520 represents a bent bone by connecting two tubular shaped display forms on one end on the axial direction of the display forms. The bone image 522 also represents the bending angle θ of the bone by a connection angle of the two tubular shaped display forms.

A subarray marker 524 is also displayed in the bone shape image 520. Four subarray markers 524 (ProbeA-1, ProbeA-2, ProbeB-1, and ProbeB-2) correspond to the subarrays A1, A2, B1, and B2 of FIG. 2, respectively. In FIG. 8, each subarray marker 524 shows a portion of the driven transducer element with a filled box, to show the position of the transducer element (a position along the axial direction of the bone).

An echo tracking switch (ET) and a numerical value of the bending angle θ (0.0537) may be displayed in the bone shape image 520. The bone image 522 may be formed with a display form of two quadrangular columns or the like. The bone image 522 may alternatively be formed with an ultrasonic tomographic or X-ray image of the bone to be measured.

The graph image 530 includes a load change graph 532 and an angle change graph 534. The load change graph 532 is a graph which shows change with respect to time of the amount of load by showing the time (Time) on the horizontal axis and the amount of load (Load) on the vertical axis. A time phase marker which shows a time phase which is set by the time setting bar 540 to be described later is shown with a broken line in the load change graph 532. In addition, a numerical value such as a maximum value of the amount of load (Max) and the amount of load of the time corresponding to the time phase marker may be displayed in the load change graph 532.

The angle change graph 534 is a graph which shows change with respect to time of a bending angle by showing time (Time) on the horizontal axis and the bending angle (Angle) on the vertical axis. A time phase marker which shows a time phase which is set by the time setting bar 540 is shown with a broken line in the angle change graph 534. In addition, a numerical value such as a maximum value of the bending angle (Max) and a bending angle of the time corresponding to the time phase marker may be displayed in the angle change graph 534.

The time setting bar 540 provide a user interface for setting time. Specifically, an examiner sets a slider 542 to a desired time by operating the slider 542 along the time setting bar 540 using a mouse or a keyboard. An adjustment button for finely adjusting time may be provided near the time setting bar 540. With this structure, the examiner can set an approximate time with the time setting bar 540 and then finely adjust the time using the adjustment button.

The time which is set by the time setting bar 540 is reflected in the graph image 530 and the bone shape image 520. That is, the time phase markers in the load change graph 532 and angle change graph 534 slide along the horizontal axis (time) direction according to the setting of the time setting bar 540, to indicate the time phase which is set by the time setting bar 540. The bone shape image 520 displays a bent state of a bone corresponding to the bending angle at the time phase which is set by the time setting bar 540.

Therefore, with the measurement result image 500, the examiner (user) can understand the bent state of the bone at a desired time phase through the bone shape image 520 by operating the time setting bar 540 while understanding the changes with respect to time of the amount of load and the bending angle by viewing the graph image 530.

Various switches such as an output switch of a measurement data file (CSV) a print output switch (Print) and a cancel switch (Cancel) may be provided in the measurement result image 500.

Figure 9:
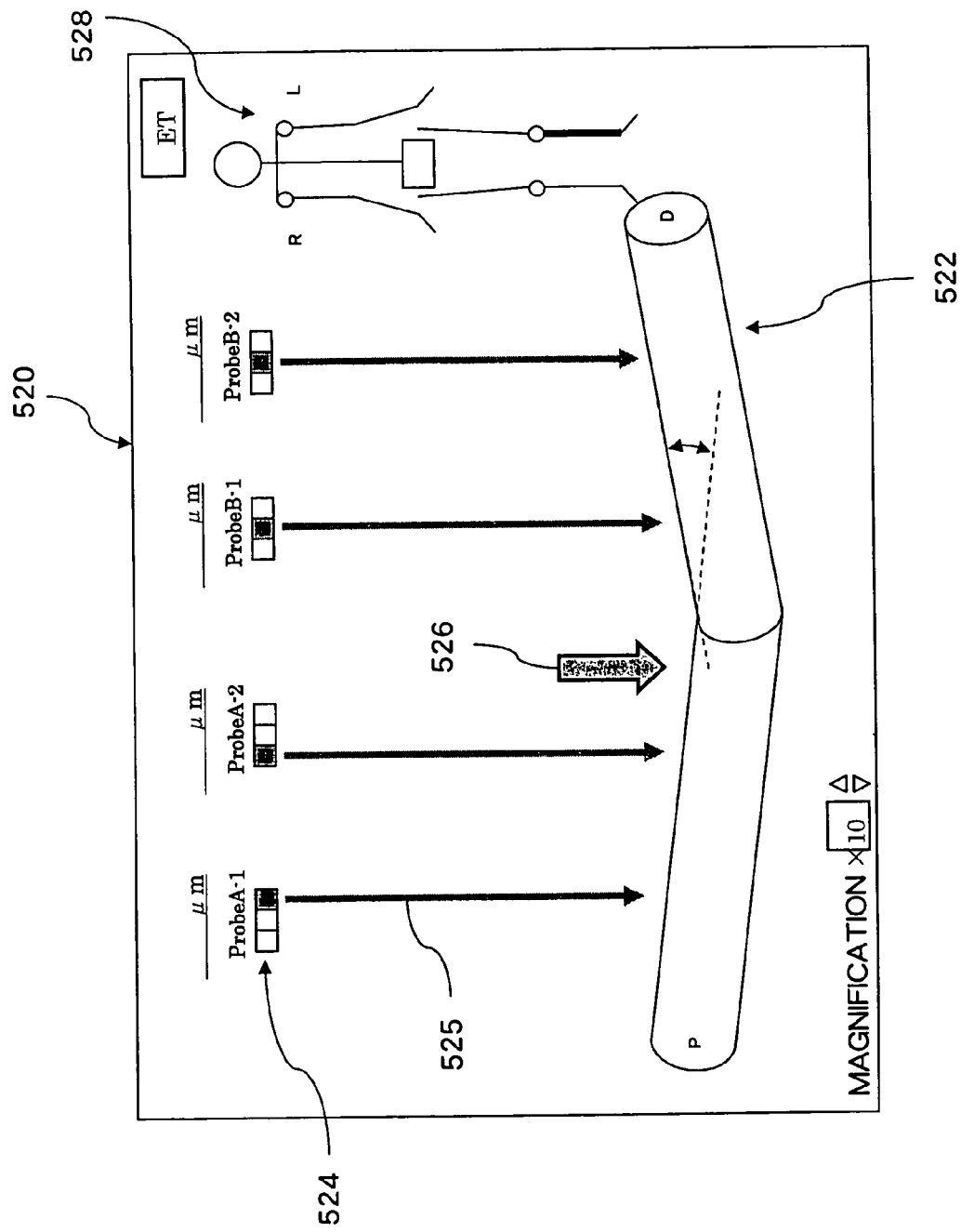
FIG. 9 is a diagram for explaining various markers displayed in a bone shape image.

FIG. 9 is a diagram for explaining various markers displayed in the bone shape image 520. As described above with reference to FIG. 8, the bone image 522 and the subarray marker 524 are displayed in the bone shape image 520. In addition, various markers such as a beam marker 525, a load position marker 526, and a bone position marker 528 may be displayed in the bone shape image 520, as shown in FIG. 9.

The beam marker 525 visually shows formation of the plurality of ultrasonic beams on a bone. In other words, the beam marker 525 represents formation of the ultrasonic beam from the subarray marker 524 showing the position of the probe towards the bone image 522 showing the bone to be measured. In the present embodiment, because four echo tracking ultrasonic beams are formed, four beam markers 525 are shown in FIG. 9.

The load position marker 526 visually shows a position and a direction of a load applied to the bone. FIG. 9 shows that a load which is approximately perpendicular to the axial direction of the bone is applied near a connection point in the bone image 522 in which two tubular shaped display forms are connected. The amount of load may be represented by a length of the load position marker 526 or the like.

The bone position marker 528 is a maker which shows a position of the bone to be measured in the subject. In other words, the bone position marker 528 schematically shows an overall skeleton of the subject, and a part of the bone to be measured in the schematically shown overall skeleton with a display form which differs from the other portions. In FIG. 9, the bone position marker 528 shows that a bone in a crus portion (such as tibia and fibula) on the left side (L) of a human who is the subject is the bone to be measured.

A marker (P) which shows a proximate side and a marker (D) which shows a distant side may be displayed in the bone image 522. In addition, a user interface for changing a magnification of display of bend for the bone image 522 may be formed in the bone shape image 520.

Figure 10:
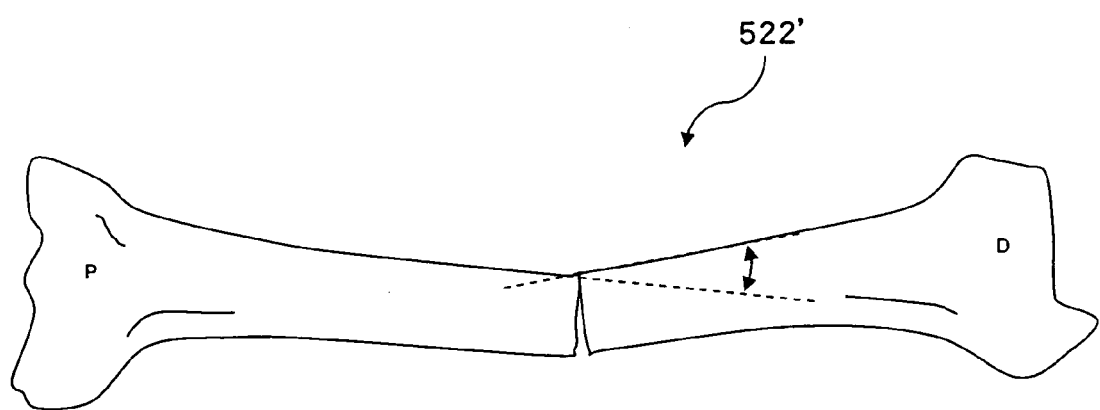
FIG. 10 is a diagram for explaining an alternative display form of a bone image.

FIG. 10 is a diagram for explaining an alternate display form of the bone image. A bone image 522 in which two tubular shaped display forms are connected to each other has been described with reference to FIGS. 8 and 9. In FIG. 10, on the other hand, a bone image 522' schematically shows an actual shape of the bone to be measured. That is, when the bone to be measured is a tibia of a human, a bone image 522' having a shape similar to the tibia of human is formed, and, when the bone to be measured is a fibula of a human, a bone image 522' having a shape similar to the fibula of human is formed. The bone image 522' is displayed in the measurement result image 500 of FIG. 8, for example, at a position of the bone image 522, in place of the bone image 522.

Figure 11:
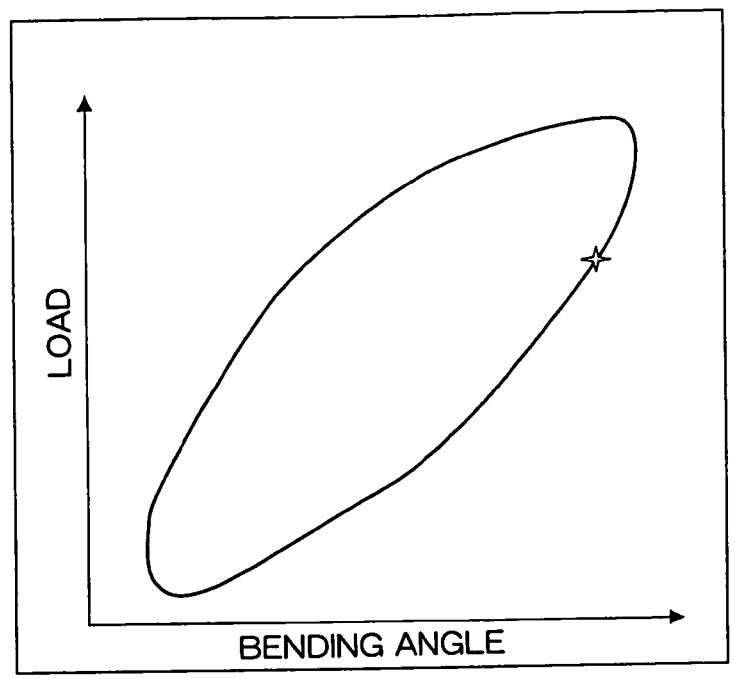
FIG. 11 is a diagram showing another preferable example display of a graph image.

FIG. 11 shows another preferred example display of the graph image. A graph of FIG. 11 shows a characteristic curve having the bending angle on the horizontal axis and the load on the vertical axis. A hysteresis property exists between the load on the bone and the bending angle. In other words, the increasing property of the bending angle of the bone when the load value is gradually increased to the maximum load value and the decreasing property of the bending angle when the load value is gradually reduced from the maximum load value do not necessarily match. FIG. 11 shows an angle characteristic when the load value is increased to the maximum load value and then reduced from the maximum load value. For example, an area within the graph which is drawn in a loop shape reflects the hysteresis property between the load value and the bending angle. The area becomes an indication for evaluating, for example, a viscoelastic component of the bone.

A star-shaped marker is displayed on the characteristic curve which is drawn in the loop shape. The marker is set, for example, corresponding to a time which is set by the time setting bar 540 of FIG. 8. In other words, the star-shaped marker is displayed in FIG. 11 at the part of the load and the bending angle corresponding to the time set by the user. The star-shaped marker moves on the loop-shaped characteristic curve according to a time changing operation by the user.

Figure 12:
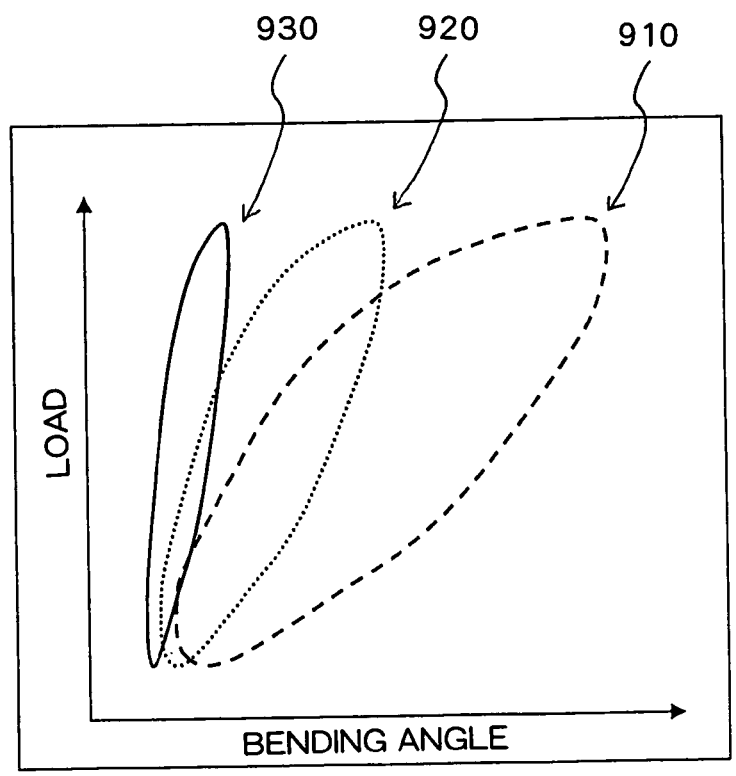
FIG. 12 is a diagram showing yet another preferable example display of a graph image.

FIG. 12 shows another preferred example display of the graph image. Similar to the graph of FIG. 11, the graph of FIG. 12 is a characteristic curve having the bending angle on the horizontal axis and the load on the vertical axis. The display form of FIG. 12 shows a state of change with respect to time of the measurement result based on a plurality of measurement data obtained at timings which differ from each other. In other words, the example display of FIG. 12 shows a plurality of characteristic curves 910, 920, and 930 obtained at different timings.

For example, measurement is executed on a same subject and under a same measurement condition, and the characteristic curve 910 is obtained based on a result of measurement on Jan. 1, 2000, the characteristic curve 920 is obtained based on a measurement result on Mar. 1, 2000, and the characteristic curve 930 is obtained based on a measurement result on May 1, 2000.

As described, the example display of FIG. 12 shows a state of change with respect to time of the measured quantity reflecting the shape of the bone. With the example display of FIG. 12, for example, it is possible to easily visually understand the process of gradual union of a fractured bone.

The above-described embodiment has the following advantages. For example, with the display forms of FIGS. 8-12, it is possible to easily imagine a deformation of a bone with respect to a load, and these display forms are effective for diagnosis of a bone fracture. In addition, these display forms become valuable information for knowing a state of a stress experienced by the bone with respect to the load. By showing the display forms of FIGS. 8-12 to the subject, it is possible to explain the measurement result to the subject in a manner understandable for the subject.

A preferred embodiment has been described. The above-described embodiment is merely exemplary, and should not be understood to be limiting the scope of the present invention. For example, it is possible to employ an embodiment in which a program is created for realizing functions such as the echo tracking processor 20, the angle calculating unit 22, the characteristic data calculating unit 24, and the display image formation unit 32 of FIG. 1 and a recording medium storing the program may be read by a computer. By operating a computer according to this program, it is possible to cause the computer to function as a bone evaluating device having the functions described above with reference to FIGS. 3-6. Alternatively, it is also possible to cause the computer to function as an image formation device which forms a display image as described above with reference to FIGS. 8-12. The display images of FIGS. 8-12 are not limited to those displayed on the display 34, and may be, for example, printed on paper. The present invention includes various modifications and changes within the scope and spirit of the present invention.

What is claimed is:

1. An ultrasound diagnosis apparatus comprising:
   a transmission and reception unit configured to form a plurality of ultrasonic beams on a target bone;
   a surface point identifying unit configured to identify a surface point corresponding to a surface of the target bone for each ultrasonic beam;
   an angle calculating unit configured to calculate a bending angle of the target bone based on a plurality of surface points; and
   a characteristic information generator unit configured to generate characteristic information which reflects a mechanical characteristic of the target bone based on a bending angle of the target bone due to an external action and form data indicating a length of the target bone and respective distances from an evaluation reference point to ends of the target bone.

2. The ultrasound diagnosis apparatus according to claim 1, wherein
   the characteristic information generator unit calculates, as the characteristic information, data corresponding to a ratio between an indication value which reflects a load applied to the target bone, the length of bone of the target bone, and the position of the evaluation reference point of the target bone, and the bending angle of the target bone due to the load.

3. The ultrasound diagnosis apparatus according to claim 1, further comprising:
a screen formation unit which forms an input screen for allowing input of a length of bone of the target bone and a position of an evaluation reference point of the target bone as the form data.

4. The ultrasound diagnosis apparatus according to claim 3, wherein
the screen formation unit forms an input screen having an image of the target bone and a cursor which moves along the image, and allows a user to input the position of the evaluation reference point of the target bone by moving the cursor to a position corresponding to the evaluation reference point according to an operation by the user.

5. The ultrasound diagnosis apparatus according to claim 1, further comprising:
an image formation unit which forms a bone shape image which visually represents a bent state of a bone according to the bending angle as an image for displaying the bending angle calculated by the angle calculating unit.

6. The ultrasound diagnosis apparatus according to claim 5, wherein
the image formation unit forms the bone shape image in which a bent bone is represented by connecting two column-shaped display forms on one end along an axial direction of the display forms and the bending angle of the bone is represented by a connection angle between the two column-shaped display forms.

7. The ultrasound diagnosis apparatus according to claim 5, wherein
the image formation unit forms the bone shape image in which an actual shape of the target bone is schematically represented.

8. The ultrasound diagnosis apparatus according to claim 5, wherein
the angle calculating unit calculates the bending angle of the bone when a load is applied to the bone, and
the image formation unit forms an angle change graph which shows change with respect to time of the bending angle by showing time on one axis and the bending angle on the other axis, and forms the bone shape image corresponding to the bending angle of a time indicated by a time marker displayed within the angle change graph.

9. The ultrasound diagnosis apparatus according to claim 5, wherein
the angle calculating unit calculates a bending angle of the bone when a load is applied to the bone, and
the image formation unit forms a load change graph which shows change with respect to time of an amount of load by showing time on one axis and the amount of load on the other axis, and forms the bone shape image of the time when the amount of load at a time indicated by a time marker displayed within the load change graph is applied.

10. An ultrasound diagnosis apparatus comprising:
a transmission and reception unit configured to form a plurality of ultrasonic beams on a bone;
a surface detecting unit configured to detect a surface point corresponding to a surface of a bone for each ultrasonic beam and detects a plurality of surface points based on a plurality of ultrasonic beams;
a shape measuring unit configured to determine a measured quantity which reflects a shape of a bone based on the plurality of the detected surface points; and
an image formation unit configured to form a bone shape image which visually represents a shape of bone as an image for displaying the determined measured quantity,
wherein the shape measuring unit determines a bending angle of bone as the measured quantity, and
the image formation unit forms the bone shape image which visually represents a bent state of a bone according to the determined bending angle,
wherein the image formation unit forms the bone shape image in which a bent bone is represented by connecting two column-shaped display forms on one end along an axial direction of the display forms and the bending angle of the bone is represented by a connection angle between the two column-shaped display forms.

11. The ultrasound diagnosis apparatus according to claim 10, wherein
the image formation unit forms the bone shape image in which an actual shape of a bone to be measured is schematically represented.

12. The ultrasound diagnosis apparatus according to claim 10, wherein
the shape measuring unit determines a bending angle of bone when a load is applied to the bone, and
the image formation unit forms an angle change graph which shows change with respect to time of the bending angle by showing time on one axis and the bending angle on the other axis, and forms the bone shape image corresponding to the bending angle of a time indicated by a time marker displayed within the angle change graph.

13. The ultrasound diagnosis apparatus according to claim 10, wherein
the shape measuring unit determines a bending angle of bone when a load is applied to the bone, and
the image formation unit forms a load change graph which shows change with respect to time of an amount of load by showing time on one axis and the amount of load on the other axis, and forms the bone shape image of the time when the amount of load at a time indicated by a time marker displayed within the load change graph is applied.

14. The ultrasound diagnosis apparatus according to claim 10, wherein
the image formation unit forms a waveform image which shows a waveform of each ultrasonic beam near the surface point and a beam position image which shows a position of each ultrasonic beam in a transmission and reception plane of the transmission and reception unit.

15. The ultrasound diagnosis apparatus according to claim 10, wherein
the image formation unit forms a display image which visually represents formation of the plurality of ultrasonic beams on the bone by displaying a beam marker which visually represents each ultrasonic beam within the bone shape image.

16. The ultrasound diagnosis apparatus according to claim 10, wherein
the image formation unit displays, within the bone shape image, a bone position marker which shows a position of a bone to be measured within a subject.

* * * * *